(12) United States Patent
Staats et al.

(10) Patent No.: US 6,648,860 B2
(45) Date of Patent: Nov. 18, 2003

(54) CONTRAST DELIVERY SYRINGE WITH INTERNAL HYDROPHILIC SURFACE TREATMENT FOR THE PREVENTION OF BUBBLE ADHESION

(75) Inventors: Peter Staats, Loveland, OH (US); William E. Bausmith, III, Batavia, OH (US)

(73) Assignee: Liebel-Flarsheim Company, Cincinnati, OH (US)

( * ) Notice: Subject to any disclaimer, the term of this patent is extended or adjusted under 35 U.S.C. 154(b) by 0 days.

(21) Appl. No.: 09/905,809

(22) Filed: Jul. 13, 2001

(65) Prior Publication Data

US 2003/0023206 A1 Jan. 30, 2003

(51) Int. Cl.[7] .......................... A61M 25/00; A61M 5/32; A61M 31/00; A61M 37/00
(52) U.S. Cl. ..................................... 604/265; 604/93.01
(58) Field of Search ................................ 604/264, 265, 604/266, 267, 268, 269, 48, 19, 93.01; 427/2.1, 2.12, 2.3, 255.6, 447

(56) References Cited

U.S. PATENT DOCUMENTS

| | | | |
|---|---|---|---|
| 3,526,583 A | 9/1970 | Hayward | 204/165 |
| 4,072,769 A | 2/1978 | Lidel | 427/38 |
| 4,533,569 A | 8/1985 | Bangs | 427/154 |
| 4,663,233 A | 5/1987 | Beavers | 428/412 |
| 5,098,618 A * | 3/1992 | Zelez | 264/1.38 |
| 5,148,311 A | 9/1992 | Beavers et al. | 359/507 |
| 5,468,560 A | 11/1995 | McPherson et al. | 428/413 |
| 5,922,161 A * | 7/1999 | Wu et al. | 156/272.6 |
| 6,017,577 A * | 1/2000 | Hostettler et al. | 427/2.12 |
| 6,102,699 A | 8/2000 | Galehr et al. | 433/90 |
| 6,193,369 B1 | 2/2001 | Valint, Jr. et al. | 351/160 H |
| 6,263,641 B1 * | 7/2001 | Odell et al. | 53/425 |

* cited by examiner

Primary Examiner—Manuel Mendez
Assistant Examiner—Mark K. Han
(74) Attorney, Agent, or Firm—Wood, Herron & Evans LLP

(57) ABSTRACT

A syringe for injecting a fluid, such as a contrast medium for radiological diagnostic imaging, is enhanced by hydrophilic treatment of interior surfaces of the syringe, reducing air bubble attachment to the syringe. Air bubbles that do form or that are drawn into the syringe fail to attach to, or readily release from, the interior surface and can be expelled prior to being used on a patient.

10 Claims, 1 Drawing Sheet

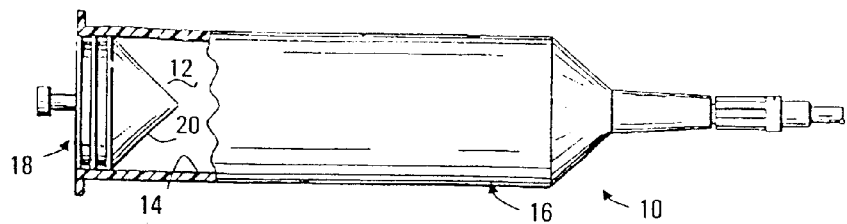
FIG. 1 *Prior Art*
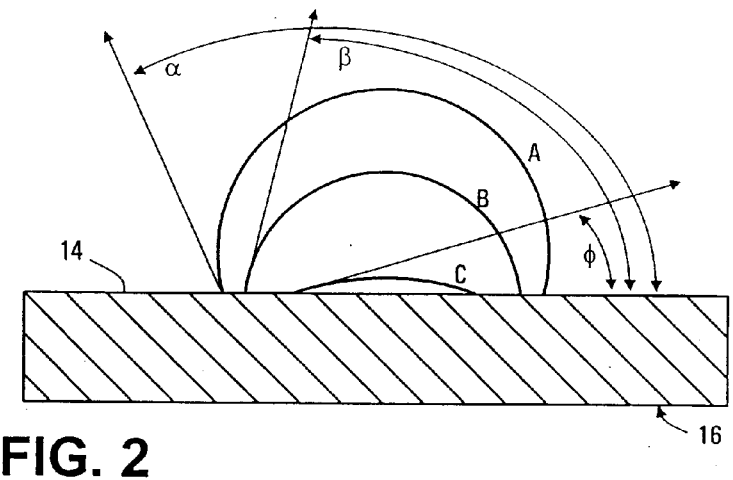
FIG. 2
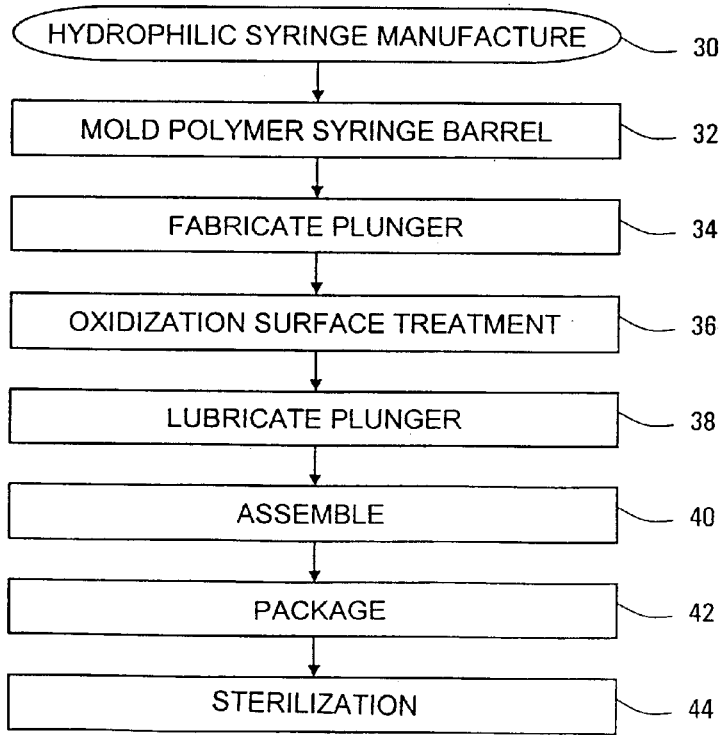
FIG. 3

CONTRAST DELIVERY SYRINGE WITH INTERNAL HYDROPHILIC SURFACE TREATMENT FOR THE PREVENTION OF BUBBLE ADHESION

FIELD OF THE INVENTION

The present invention relates to manufacturer of polymer syringes for clinical use with patients.

BACKGROUND OF THE INVENTION

Medical professionals are aware of the hazards of injury and death to patients from air bubbles in the blood. An air embolism, also called a a gas embolism, is a blockage of an artery or vein by an air bubble. Air can be introduced into the blood vessels during surgery or traumatic accidents. One example of an air embolism is the "bends", a common hazard of underwater diving while breathing compressed air. Another type of traumatic embolization occurs when lung tissue is ruptured; bubbles of air pass from the alveoli (air sacs) of the lungs into nearby capillaries and veins. The air bubbles are then carried into the heart, where, if trapped, they can cause myocardial infarction, the destruction of tissue in the heart muscle; usually, however, the air rises to the brain. The consequent blockage of vessels carrying blood to the brain starves this tissue of its vital blood supply. Nervous tissue becomes irreversibly damaged after about five minutes of oxygen and nutritional starvation; convulsions, unconsciousness, respiratory difficulties, and death may ensue.

In view of the hazards of air embolisms, great care is taken to avoid introduction of air into the blood stream during surgical procedures. For instance, intravenous (IV) catheters are arranged so that air will not be entrained into the vein during use. Injection of medicines and inoculations by needle are performed after air is expelled from the syringe. These measures minimize inadvertent injection of air into the patient. Even when air is accidentally injected, generally no harm occurs due to the small amount of air involved and the site of the injection. The patient's body is often capable of absorbing the gas before it reaches a critical part of the body such as the heart or brain. However, the presence of air in a syringe or catheter is still a cause for apprehension.

Injection of contrast medium into a vein or artery is a specific example of a surgical procedure wherein great care is exercised in avoiding the introduction of air bubbles. As an example, angiography, also called arteriography, is the diagnostic imaging of arteries and veins, using radiological modalities such as x-ray, ultrasonics, and magnetic resonance imaging (MRI). To differentiate circulatory structures from the surrounding organs and to perform dynamic studies of circulation flow, often contrast media is injected into vessels. The contrast media is opaque to the imaging modality (e.g., x-ray) or otherwise enhances the return (e.g., MRI). Powered injection of contrast medium during angiography is often desirable. A power injector provides a predictable rate of flow, generates sufficient force to inject viscous contrast media, and allows medical personnel to be further removed from the imaging system.

Avoiding introduction of air to the blood vessel is a key part of the design and operating procedures for power injectors. First, these angiographic procedures generally inject a relatively large quantity of contrast media at a significant pressure, thus compressing any air bubbles during injection. The air bubbles expand after injection into a large vessel, and thereafter can quickly reach critical circulatory structures in the body. Consequently, the syringes are filled and air removed prior to preparing the patient for catheterization. The plunger end of the syringe is elevated during injection so that any remaining air bubbles tend to stay in the syringe during injection. Keeping the air bubbles in the syringe is assisted by the rate of flow within the syringe. Bubbles that form on interior surfaces are subject to low rates of flow and thus tend to remain until mechanically wiped by the plunger, accumulating at the rear of the syringe during the procedure.

Thus, while the design and procedures minimize the risk of air embolisms, there is an inconvenience involved in preparing the injector. Not only do the medical professionals have to spend time removing air bubbles as a good clinical practice, often small amounts of remaining air bubbles that pose no risk are removed to avoid apprehension by the patient. The additional time required to remove air bubbles slows the process of imaging and increases the staffing required to perform the imaging. Since the equipment for diagnostic imaging is expensive, even small delays to the process decrease the usage of the diagnostic imaging facility, thus increasing the cost per patient to amortize the fixed costs for equipment and the facility.

Therefore, a significant need exists for a syringe for injecting fluids into the body that has a reduced tendency to accumulate air bubbles.

SUMMARY OF THE INVENTION

The present invention addresses these and other problems in the art with a syringe and a method of producing a syringe wherein the interior surface of the syringe is treated with a hydrophilic surface treatment to reduce attachment of air bubbles when injecting a water-based fluid. Thereby the time required to prepare the syringe is reduced and patient apprehension reduced.

The above and other objects and advantages of the present invention shall be made apparent from the accompanying drawings and the description thereof.

Brief Description of the Drawings

FIG. 1 shows a syringe consistent with aspects of the present invention;

FIG. 2 is a cross-sectional depiction of illustrative fluid contact angles with respective hydrophobic, untreated, and hydrophilic surfaces; and FIG. 3 is a sequence of operations for fabricating a polymeric syringe suitable for injection of contrast media with a power injector.

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF SPECIFIC EMBODIMENTS

A syringe 10 for injecting a fluid 12, such as a contrast medium for radiological diagnostic imaging, is enhanced by hydrophilic treatment of an interior surface 14, reducing air bubble formation and attachment to the syringe 10. Air bubbles that do form or that are drawn into the syringe 10 fail to attach to, or readily release from, the interior surface 14 and can be expelled prior to being used on a patient. Thus, the time required to prepare the syringe 10 is reduced and patient apprehension is avoided.

With particular reference to FIG. 1, a syringe 10 is fabricated in a manner such as disclosed in the commonly owned U.S. Pat. Nos. 5,855,568 to Battiato et al. and U.S. Pat. No. 5,902,276 to Namey, Jr., both of which are hereby incorporated by reference in their entirety. Advantageously, a conventional syringe barrel 16 is molded from a transparent polymer with properties appropriate for the pressures and sterilization required for medical use. For instance, a co-polyester material is used in "ILLUMENA™" syringes 10 for injecting contrast media (e.g., OPTIRAY™ Contrast Media) with an ILLUMENA™ power injector, all available from the Liebel-Flarscheim Group of Mallinckrodt Inc., Cincinnati, Ohio. Other suitable materials include a polypropylene material, as well as other materials known to those skilled in the art having the benefit of the present disclosure. A plunger 18 of the syringe 10 presents a soft rubber surface 20 to the fluid 12 and to the interior surface 14.

Polymers such as polypropylene and co-polyester generally have a low surface-attractive force for water-based fluids. The generally low surface energy provides limited polar interaction for the interior surface 14 to attract the water-based fluid 12. Thus, air bubbles tend to readily attach to the interior surface 14. The term "hydrophilic" is used to refer to a high surface energy that attracts the water-based fluid 12 and thus minimizes air bubble attachment. The term "hydrophobic" is used to refer to a low surface energy that provides less attraction for the water-based fluid 12, and thus increases air bubble attachment.

Oxidization of the interior surface 14 advantageously provides a hydrophilic reaction property, reducing air bubble attachment to polymer syringes 10. Various techniques of oxidization are known: corona treatment, oxidizing acids (e.g., chromic acid), flame treatment, and oxygen plasma treatment. Also, physical roughening or etching can be employed to increase surface area, so that the surface can then be coated with a thin layer of a primer with hydrophilic properties.

Oxygen plasma surface treatment was used in an illustrative treatment of conventional co-polyester and polypropylene syringes for determining air bubble attachment. Oxygen plasma surface treatment includes a closed chamber filled with air or an enriched oxygen atmosphere that is energized into a plasma by a radio frequency electromagnetic field. Oxygen plasma surface treatment lends itself to precise control of the oxidization process (e.g., temperature, atmosphere content, strength and distribution of the RF field, duration of exposure). Also, oxygen plasma surface treatment may be used on the otherwise difficult to reach interior surface 14 of the syringe 10. However, it will be appreciated by those skilled in the art having the benefit of the present disclosure that various materials for a syringe 10 may be selected as well as various techniques for providing a hydrophilic interior surface 14 consistent with aspects of the invention.

One way to quantify the degree to which the interior surface 14 is hydrophilic or hydrophobic is to measure contact angle of fluid/surface formed thereon. In addition, inspection may be made of the size and number of air bubbles attached to the interior surface 14 and how readily these bubbles detach with time or with movement of the syringe 10. With particular reference to FIG. 2, a depiction is made of measuring contact angle fluid droplet "A" formed on a hydrophobic interior surface 14 of the syringe barrel 16, fluid droplet "B" on an untreated interior surface 14, and fluid droplet "C" on an advantageously hydrophilic interior surface 14.

The fluid droplet A is weakly attached to the hydrophobic interior surface 14, thus allowing a larger, more spherical fluid droplet to form. Thus, a contact angle "α", tangential to the fluid droplet at the surface 14, is large. The fluid droplet B for an untreated surface 14 is smaller and thus has a smaller contact angle "β". The bubble C on the hydrophilic surface 14 is smaller still, forming the smallest contact angle "φ".

An experiment to show the advantageous reduction of air bubble attachment was performed using six co-polyester syringes. Two syringes were given a hydrophobic surface treatment in a plasma chamber. Two syringes were given a hydrophilic surface treatment by using oxygen plasma in the plasma chamber. Two syringes were left untreated. Each of the resulting six syringes were sequentially filled with each of four fluids: water, 160, 240, and 350 OPTRAY™ contrast media, with contact angle measured for each fluid for each syringe as shown in Table 1.

TABLE 1

| Contrast media | Hydrophobic (α) | Untreated (β) | Hydrophilic (φ) |
| --- | --- | --- | --- |
| Water | 103 degrees | 77 degrees | 7 degrees |
| 160 OPTIRAY ™ | 110 degrees | 75 degrees | 8 degrees |
| 240 OPTIRAY ™ | 106 degrees | 71 degrees | 11 degrees |
| 350 OPTIRAY ™ | 84 degrees | 73 degrees | 16 degrees |

As will be apparent from the resulting contact angle measurements, the hydrophilic surface treatment resulted in a significant reduction in contact angle for each of the four fluids of about 80–90%.

The advantage of the low contact angle of about 7–16 degrees for the hydrophilic surface 14 was shown by subsequently agitating each syringe 10 with each type of fluid 12 and with a volume of air. The agitated syringe 10 was allowed to set. By inspection, it was apparent that the hydrophobic syringes 10 contained more and larger bubbles than the others, the bubbles tended to cling to the sides of the syringe indefinitely unless wiped off by the action of the plunger 20. The untreated syringes were similar, but to a lesser degree. The hydrophilic surface treated syringes showed few bubbles that remained on the interior surface 14 when the syringe 10 was allowed to set. These bubbles readily detached when the syringe was gently rotated.

The use of the present invention is illustrated by FIG. 3, wherein a hydrophilic syringe manufacturing process 30 is performed by molding a polymer syringe barrel (block 32). A plunger is also fabricated (block 34). Oxidization surface treatment such as by oxygen plasma, is given to the barrel and in some instances also to the plunger (block 36), resulting in a hydrophilic interior surface. Depending on the materials of the syringe and the intended fluid to be injected, the interior of the barrel and/or the periphery of the plunger may be lubricated (block 38). Then the syringe is assembled by inserting the plunger into the barrel (block 40). The syringe is packaged (block 42) and sterilization is performed (block 44).

By virtue of the foregoing, a syringe having a hydrophilic interior surface advantageously reduces air bubbles formed when filled with a water-based fluid such as contrast media, decreasing the time involved in providing diagnostic imaging services.

While the present invention has been illustrated by a description of various embodiments and while these embodiments have been described in considerable detail, it is not the intention of the applicants to restrict or in any way limit the scope of the appended claims to such detail.

Additional advantages and modifications will readily appear to those skilled in the art. For example, syringes of other types of material such as glass may advantageously be treated to be more hydrophilic. As a further example, the plunger 18 may be connected to a piston arm forming a piston for manual injection. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A method of reducing air bubbles in syringes used to inject fluids into the body of animals, comprising:

hydrophilic surface treating an interior surface of a syringe barrel adapted to contain a fluid without the addition of a coating; and assembling a syringe by inserting a plunger into the syringe barrel, wherein when a fluid is contained in the syringe barrel, the fluid will be in direct contact with the interior surface.

2. The method of claim 1, further comprising:

oxidation surface treating the plunger.

3. The method of claim 1, wherein hydrophilic surface treating comprises oxidation surface treating.

4. The method of claim 3, wherein oxidation surface treating comprises oxygen plasma surface treating.

5. The method of claim 3, wherein the syringe barrel comprises material selected from the group consisting of polypropylene, co-polyester, and combinations thereof.

6. The method of claim 1 wherein the hydrophilic surface treating results in an interior-surface fluid contact angle of about 7 degrees.

7. The method of claim 1 wherein the hydrophilic surface treating results in an interior-surface fluid contact angle in a range of from about 7 to about 16 degrees.

8. A syringe assembly for injecting a fluid into the body of an animal, comprising:

a hollow cylindrical syringe barrel adapted to contain a fluid and including an open rearward end, a forward end having a discharge opening, and an uncoated intervening hydrophilic interior surface; and a plunger inserted in the open rearward end, wherein when a fluid is contained in the syringe barrel, the fluid will be in direct contact with the interior surface.

9. The syringe assembly of claim 8, wherein the hydrophilic interior surface has a fluid contact angle of about 7 degrees.

10. The syringe assembly of claim 8, wherein the hydrophilic interior surface has a fluid contact angle in a range of from about 7 to about 16 degrees.

* * * * *

UNITED STATES PATENT AND TRADEMARK OFFICE
CERTIFICATE OF CORRECTION

PATENT NO. : 6,648,860 B2
DATED : November 18, 2003
INVENTOR(S) : Bausmith et al.

It is certified that error appears in the above-identified patent and that said Letters Patent is hereby corrected as shown below:

<u>Column 1,</u>
Line 8, "The present invention relates to manufacturer of" should read -- The present invention relates to manufacture of --.
Line 15, "also called a a gas" should read -- also called a gas --.

<u>Column 2,</u>
Line 42, "Brief Description of the Drawings" should read
-- BRIEF DESCRIPTION OF THE DRAWINGS --.

Signed and Sealed this

Ninth Day of March, 2004

JON W. DUDAS
*Acting Director of the United States Patent and Trademark Office*